United States Patent
Zelechonok (12)

(10) Patent No.: US 6,257,052 B1
(45) Date of Patent: Jul. 10, 2001

(54) PUMP, SAMPLE FEED AND VALVING FOR HIGH PERFORMANCE LIQUID CHROMATOGRAPHY (HPLC)

(75) Inventor: Yury Zelechonok, Northbrook, IL (US)

(73) Assignee: Digichrom, Inc, Northbrook, IL (US)

( * ) Notice: Subject to any disclaimer, the term of this patent is extended or adjusted under 35 U.S.C. 154(b) by 0 days.

(21) Appl. No.: 09/348,735

(22) Filed: Jul. 6, 1999

(51) Int. Cl.[7] .............................. B01D 15/08; G01N 1/20; F04B 9/14; F04B 41/06
(52) U.S. Cl. ...................... 73/61.56; 73/61.59; 73/64.56; 73/864.16; 417/63; 417/494
(58) Field of Search ................................ 73/61.56, 61.59, 73/64.56, 863.83, 864.35, 864.16; 417/2, 63, 44.8, 546, 459, 462, 494

(56) References Cited

U.S. PATENT DOCUMENTS

| | | | |
|---|---|---|---|
| 3,847,507 | * | 11/1974 | Sakiyama et al. ..................... 417/22 |
| 3,922,115 | * | 11/1975 | Coe et al. ............................. 417/374 |
| 3,975,946 | * | 8/1976 | Ball et al. .......................... 73/61.1 C |
| 4,045,343 | * | 8/1977 | Achener et al. ..................... 210/101 |
| 4,102,782 | * | 7/1978 | Saito et al. ......................... 210/31 C |
| 4,233,156 | * | 11/1980 | Tsukada et al. ..................... 210/101 |
| 4,406,158 | * | 9/1983 | Allington .......................... 73/61.1 C |
| 4,883,409 | * | 11/1989 | Strohmeier et al. .................. 417/43 |
| 4,939,943 | * | 7/1990 | Strohmeier et al. .............. 73/864.21 |
| 4,980,296 | * | 12/1990 | Fisciani et al. ....................... 436/161 |
| 5,217,590 | * | 6/1993 | Lauer et al. ....................... 204/180.1 |
| 5,637,208 | * | 6/1997 | Dourdeville ........................... 210/90 |
| 5,777,213 | * | 7/1998 | Tsukazaki et al. .................. 73/61.52 |

* cited by examiner

Primary Examiner—Hezron Williams
Assistant Examiner—David J. Wiggins
(74) Attorney, Agent, or Firm—Charles F. Lind (57) ABSTRACT

The disclosed syringe pump and valve assembly utilizes a cylindrical housing having a piston axially moved therein for defining a pump chamber, where the housing is mounted to rotate about its longitudinal axis. A port seat is disposed concentrically of this axis spaced from one housing end, and a seal/valving member has one face seated slidably on the port seat and has its opposite face exposed to the pump chamber. Connectors serve to communicate separate liquid lines to separate respective ports on the port seat, which the seal/valving member first face overlies. The seal/valving member has through opening and/or radial or arcuate channels operable in different rotational member positions to selectively isolate or communicate the lines relative to one another and/or the pump chamber. The seal/valving member is designed to rotate in unison with the housing, and mechanism rotates the housing to locate the seal/valving member as required. The piston has spaced seals, defining a chamber therebetween, suited to receive liquid for flushing the pump chamber housing wall. A separate plunger projected into the pump chamber is drawn within the piston, reducing the pump chamber volume increase upon unit piston withdrawal for greater fill cycle accuracy.

9 Claims, 9 Drawing Sheets

PUMP, SAMPLE FEED AND VALVING FOR HIGH PERFORMANCE LIQUID CHROMATOGRAPHY (HPLC)

BACKGROUND OF THE INVENTION

Liquid chromatography involves the spatial separation of different sub phases (compounds or components) of a sample due to the different affinity of these sub phases with an absorbent. A typical liquid chromatography system might comprise a separation column filled with the absorbent (such as very fine powder, for example), a mechanism for discharging a liquid sample, a pump for forcing one or more liquid solvents and the liquid sample to and through the column, and a detector sensitive to different physical characteristics of the sub phases as such are then passed through the column. Due to different respective affinity rates (absorption and desorption) of the different sample sub phases with the absorbent, these sub phases will be penetrated through the column and absorbent therein at different rates. This provides that the sub phases become isolated and axially spaced out as narrow bands, sequentially and separately passing the detector to be identified along with the possible determination of each's percentage within the sample. Generally only a small quantity of liquid sample need be used (a few mcls), and the volume of the column likewise can be small (perhaps only a few mls). It is preferred to pump the solvent to high pressures to pass at an accurate and substantially steady flow rate through the sample and into the column.

Thus, a typical analytical high performance liquid chromatographic system (HPLC) might be comprised of a high pressure pump, a sample injector, a column and a detector in a serial flow connection to a waste vessel. The pump is suited to deliver liquid solvent and sample to the column at pressures typically in the 500–4000 psi range. The injector allows the introduction via a syringe or the like of the liquid sample into the solvent stream while maintaining the high pressures in the system. The column causes a major pressure drop and provides for the above noted axial separation of desired components or analytes from the complex sample form. The detector distinguishes the analytes separated from the sample, yielding information of the existence, concentration and identity of such analytes in the sample.

My patent application Ser. No. 08/876,568, now U.S. Pat. No. 5,920,006 issued on Jul. 6, 1999, disclosed a High Performance Liquid Chromatography (HPLC) pumping, sample delivery and valving system oriented toward efficient use of small microbore short columns, satisfying the increasing trend toward converting HPLC methods to use less solvent and run faster. The system is compact and essentially unitary for space efficiency and ease of movement and set-up, is lightweight and inexpensive to make and use, and yet is reliable, accurate and versatile in use, and further will have an expected extended service life with minimal solvent leakage or potential damaging of the pump.

Thus, my patented system provides syringe type liquid delivery, with steady accurately controlled flow that could be reproduced for comparable test runs and reliable test conformations. It has a built-in injector port and mixing tee, eliminating many parts needed in other HPLC systems, and has positive valving (no check valves). The valving is powered by the pump powering motor, and its valving design minimizes wear and a need for frequent repair or replacement. Its low costs and convenience and simplicity of use can encourage HPLC participation by users having limited capital budgets, and multiple units can add HPLC system versatility. Its compactness and ease of set up and use can allow possible shipments for field use or for repair or maintenance, and/or for use as an optional OEM part in other LC or liquid handling systems. Its single stroke pumping capacity could satisfy solvent needs to complete most test runs (for example, 5 ml, to complete a 100 minute test run through a 1 mm ID column or a 25 minute test run through a 2 mm ID column), and could thereafter be easily and rapidly refilled for the next test run. Should extra volume capacity be needed, or for gradient elution tests, two or three like pumping and valving devices could be connected together as a unified system for doubling or tripling solvent volume or types.

SUMMARY OF THE INVENTION

This invention improves on my patented HPLC apparatus, with new structures for metering or valving the sample relative to or from the pump, for powering the valving structures, for sealing and flushing the pump cylinder after the operating cycles, and for mounting concentric structures with minimum misalignments.

One object of this invention is to provide an HPLC pump with a valving arrangement suited for selectively connecting the sample and solvent with a pump chamber, and also then with a column, and for shifting the valving arrangement independently of the actuation of the pump.

Another object of this invention is to provide an HPLC pump with a multiple area pump plunger or piston that will be operated in two different pumping configurations, the first being suited during a conventional pressure generation and sample discharging run cycle and the second being of a significantly smaller pumping capacity suited for accurately drawing minute quantities of the sample from a sample vial or the like, in the mode of a syringe, and then for directing the sample to the column.

Yet another object of this invention is to provide an HPLC pump having a pump chamber housing and pump chamber seal that are constrained to move with only limited axial play against and relative to the valving arrangement, the housing having therein an axially shifted piston for defining a pump chamber and being rotatable about its longitudinal axis operable to shift the valving arrangement, and spring means suited to maintain a minimum tightness of the valving arrangement and seal with this axial play while the contained liquid pressures in the pump chamber during use automatically increase the tightness of the valving arrangement and seal.

A still further object of this invention is to provide an HPLC pump having a pump chamber seal of a single piece and having no mechanical connections relative to the pump chamber housing, for ease of assembly and for improved operation.

BRIEF DESCRIPTION OF THE DRAWINGS

These and other objects, features or advantages of the invention will be more fully understood and appreciated after consideration of the following description of the invention, which includes as a part thereof the accompanying drawings, wherein:

FIGS. 3 and 4 are center sectional views of different parts of the pump of

DETAILED DESCRIPTION OF PREFERRED EMBODIMENTS OF THE INVENTION

As my above mentioned U.S. Pat. No. 5,920,006 illustrates a related invention entitled HIGH PERFORMANCE LIQUID CHROMATOGRAPHY and is copending herewith, it is incorporated by references herein for details of similar components, systems or background not illustrated or explained fully herein.

Figure 8:
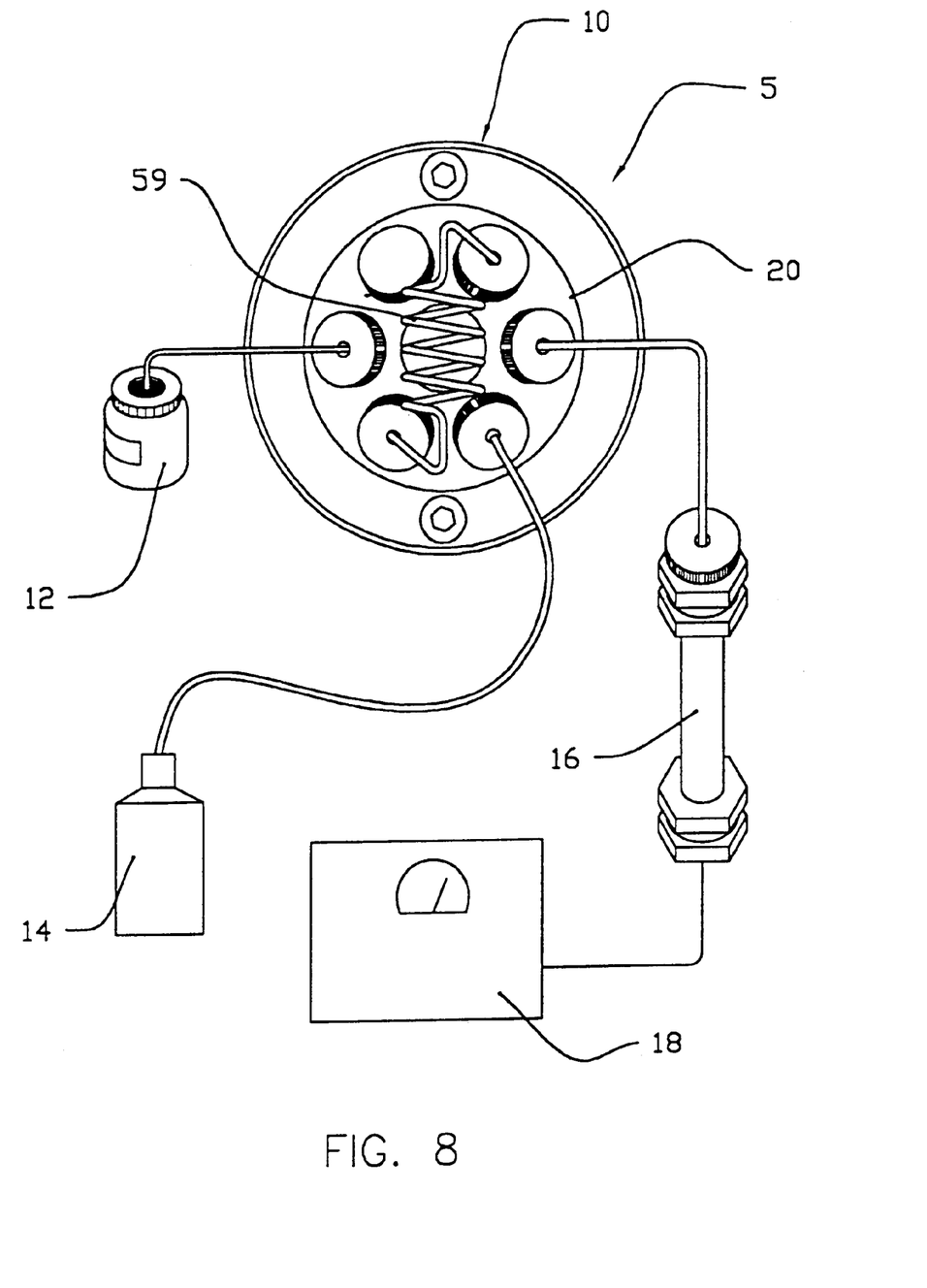
FIG. 8 is an exterior view of a 6-port valving arrangement suited for use in disclosed HPLC pump.

A typical HPLC (high pressure liquid chromatographic) system or circuit 5 (illustrated in FIG. 8) might have a pump 10, a bottle 12 or syringe for holding liquid sample to be tested, a bottle 14 or like container for holding solvent to be used in the test, a column 16 through which sample and solvent liquids are passed, a detector 18 for sensing sub phases separated out in the column 16, and valving structures 20 for connecting the components together as needed. With this broad overview, details of the pump 10 will now be given.

The pump 10 has a frame structure 22 with an open-ended cylinder housing 24 supported by sleeve bearing 23 to be rotated about its longitudinal center axis relative to the frame structure 22. A reversible drive motor 26 connected via a gear train 28 ending at gear 29 fixed to the cylinder housing operates to rotate the housing in either direction. The valving structure 20 is comprised in part of a seal/valving member 31 fixed to and effectively closing one end of the cylinder housing 24.

A cooperating piston or plunger assembly 33 is positioned in the cylinder housing 24 to be reciprocated therein, providing a variable volume pump chamber 34 at the housing end closed by the seal and valving member 31. The piston assembly 33 is connected to a lead screw 35, and a cross pin 37 fixed relative to the screw 35 and fitted through frame slots 38 allows only axial movement of the screw and no screw rotation. Rollers or other anti-friction means can be provided on the cross pin ends for minimizing drag upon the generated axial screw movement. A drive member 40 of a conventional ball nut mechanism is rotatably supported by a single combination bearing 42 (carrying both axial thrust and radial forces) relative to the frame structure 22 adjacent the open pump cylinder end. The drive member 40 is operatively coupled to the screw 35 by conventional linkages (balls fitted between the screw threads and threads on the drive member, not shown), whereby rotation of the drive member 40 causes axial movement of the screw 35. A reversible drive motor 46 is connected via a gear train 48 ending at gear 49 fixed to the drive member 40, operable to move the screw and connected piston assembly 33 within the cylinder housing 24 for operation of the pump 10. Wave spring 51 and thrust roller bearing 52 are confined between the gears 29, 49 to allow independent rotation of the gears concentrically of the screw 35 and to bias the gears and related cylinder housing 24 and drive member 40 axially apart and against the containing valving structure 20 and bearing 42.

Even though the piston assembly 33 and pump cylinder housing 24 fit together or cooperate quite snugly in a leakproof manner, these components can be rotated and shifted axially relative to one another. Thus, rotation of the drive member 40 will axially shift the screw 35 and pump piston 33 relative to the cylinder 24 operable for changing volume of the pump chamber 34, and rotation of gear 29 will rotatably shift the cylinder housing 24 relative to the valving structure 20.

The seal/valving member 31 forming part of the valving structure 20 will be larger than the cylinder housing cross section, with an annular narrow wall lip 55 protruding from the chamber side and having an exterior diameter sized slightly larger than the inside chamber bore of housing 24, suited to be pressed tightly into the cylinder bore to close the cylinder housing end. With an overlap of the lip 55 that is snuggly fit inside of the cylinder housing bore by at least several and up to possibly ten millimeters, the slight radial flex of the lip tends to seal the seal/valving member 31 more tightly as needed relative to the housing 24 upon pressure increases in the pump chamber. The seal/valving member 31 can be formed as the single piece by machining, molding or a combination of both, of durable material such as plastic.

The seal/valving member 31 also has opposed faces 62F and 62P: face 62F cooperating against a port seat formed on the frame structure 22 and the face 62P being directly exposed to fluid in the pump chamber 34, with pump face 62P being slightly larger than the frame face 62F. The longitudinal or central axes of the cylinder housing 24, screw 35, opposed seal faces 62F and 62P and the port seat might all coincide.

Figure 1:
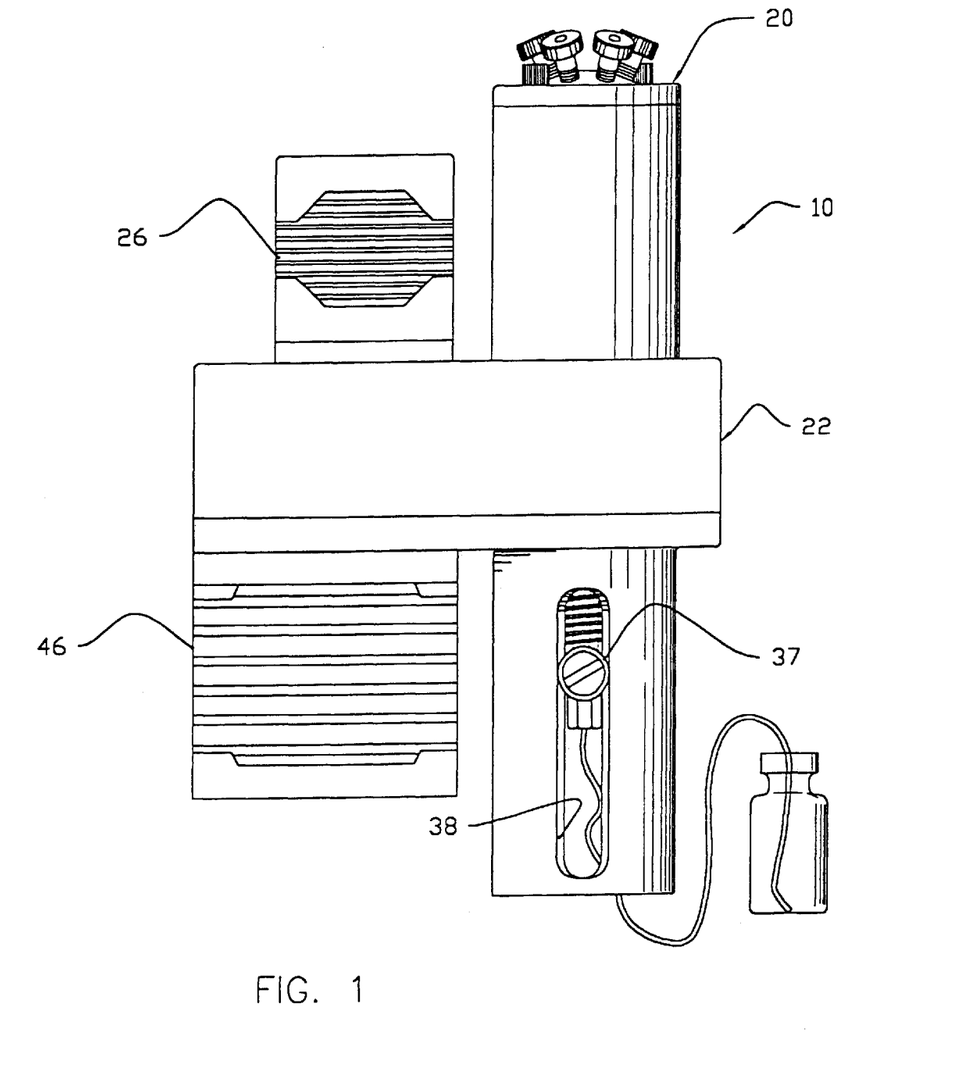
FIG. 1 is an elevational view of a HPLC pump formed according to the subject invention.
Figure 2:
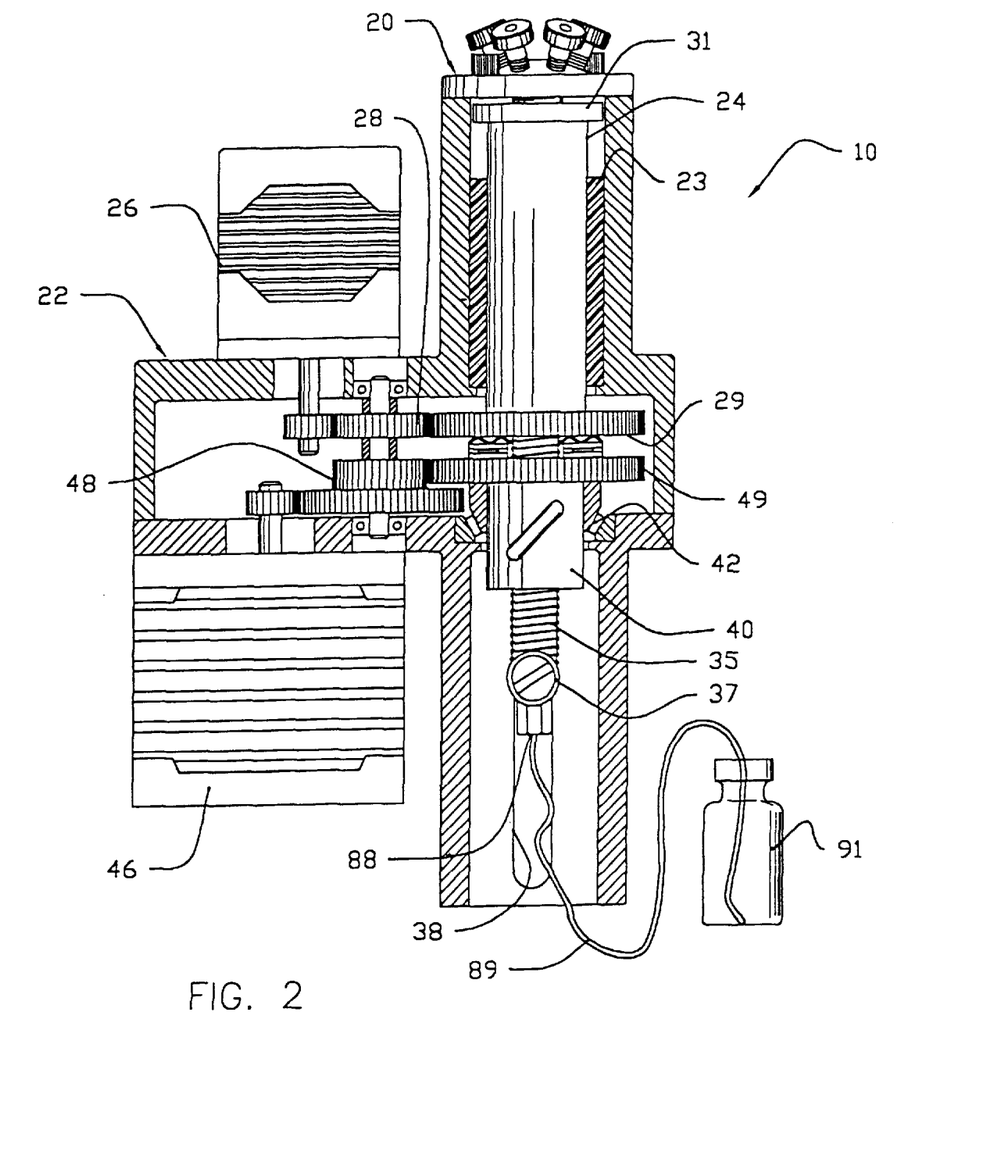
FIG. 2 is a center sectional view of the pump of FIG. 1.
Figure 3:
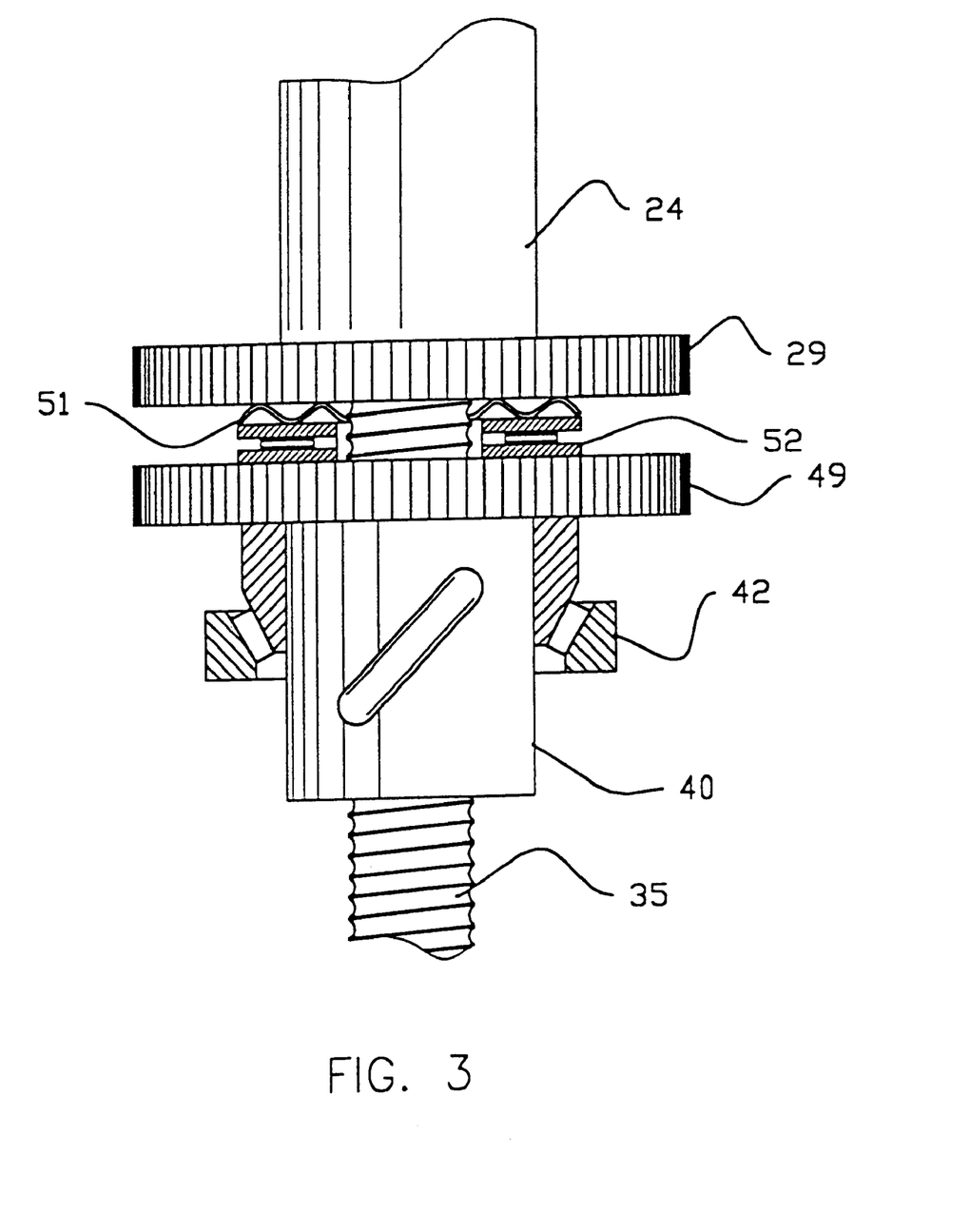
Figure 4:
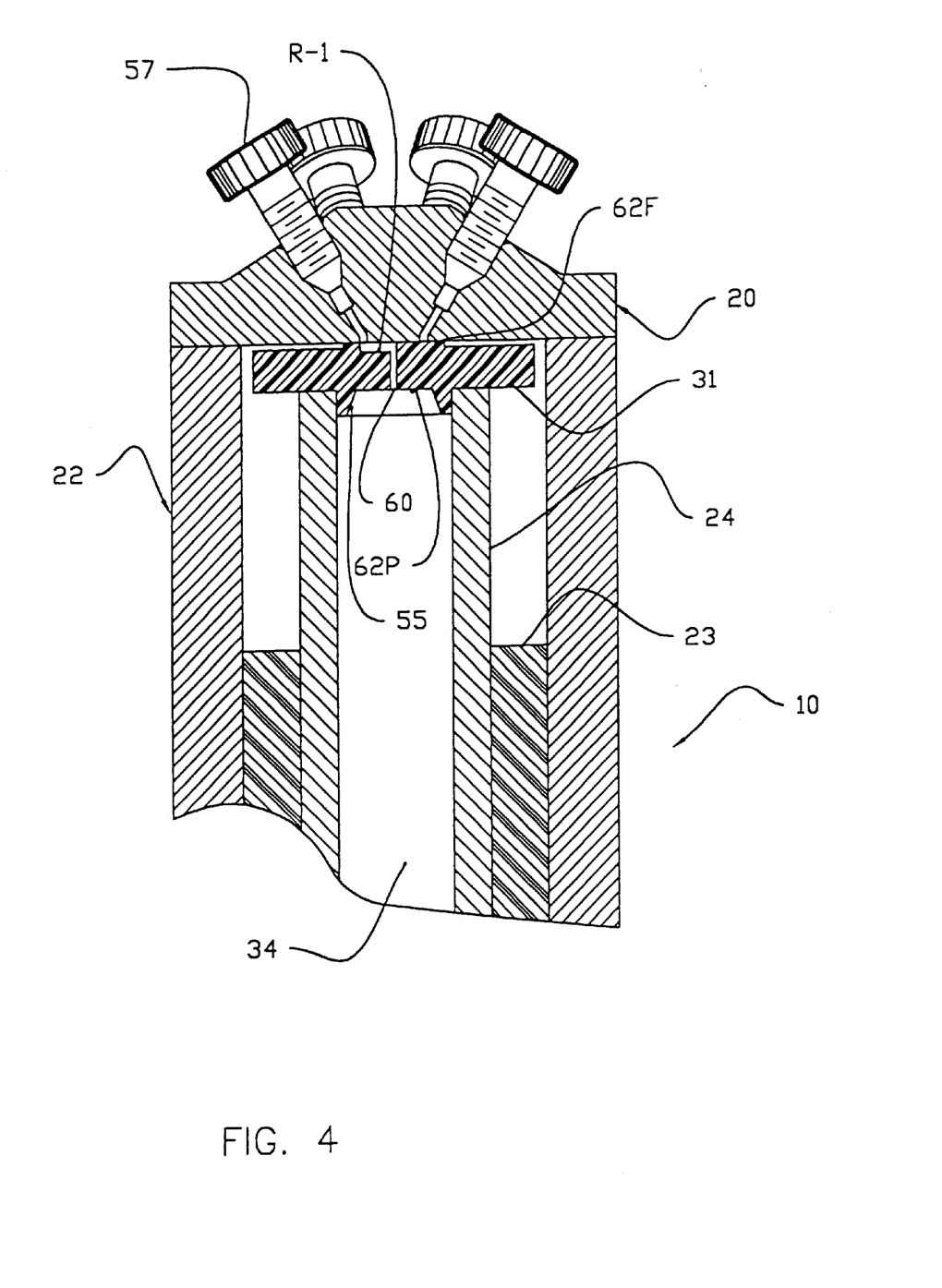

The frame port seat might typically have six ports (one being capped and thus not shown or identified) equally spaced circumferentially (at 60 degree spacings) around and equally spaced radially from the longitudinal axes of the cylinder housing 24, etc. The ports communicate via internal passages (only two being shown in FIG. 4) in the frame structure with the respective exposed threaded fittings 57. In FIGS. 9A, 9B, 9C and 9D, possible locations of the several ports are identified as for the liquid sample (10), the solvent (14) and column (16) respectively; and such correspond in FIG. 8 to the routing of communicating lines between the exposed fittings and the corresponding components. Further, two ports are identified as "loop 1" and "loop 2", and such are connected together by exterior tubing 59 via appropriate fittings.

Figure 5A:
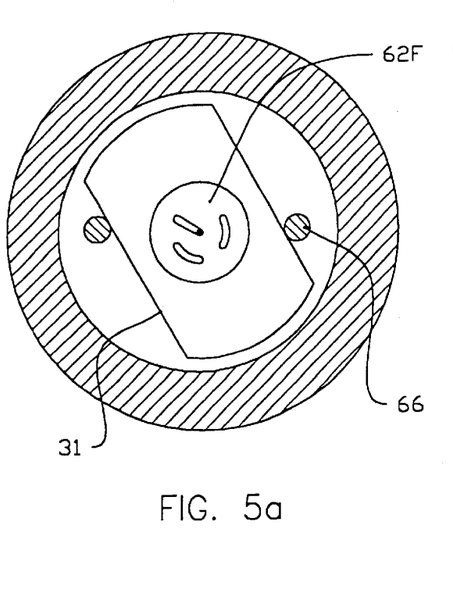
FIGS. 5A, 5B are sectional views taken generally from line 5—5 in FIG. 5C illustrating different operative positions of the valving arrangement used in the illustrated pump.
Figure 5B:
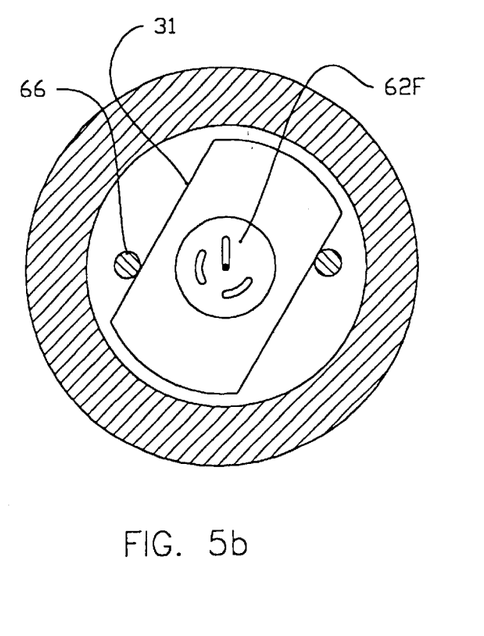
Figure 5C:
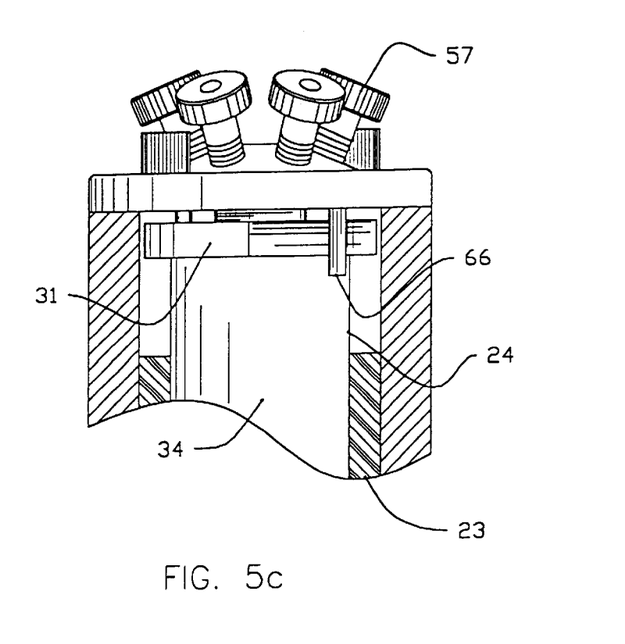
FIG. 5C shows one of the positions in a sectional view.

On the seal/valving member 31, specifically the face 62F that cooperates against the frame structure port seat has two opposite adjacent channels C-1 and C-2 each extended over approximately a 60 degree arc, the channels being located to have approximately 60 and 180 degree spacings therebetween. A single radial channel R-1 is illustrated also, extended from a center bore 60 to a remaining annular groove location spaced 60 degrees approximately from channel C-2. The center bore 60 opens to the pump chamber 34. With these 60 degree channels, it might be desirable to limit the rotation of the housing and seal/valving member 31 by means of locator pins 66 (illustrated in FIGS. 5A, 5B, 5C) that will be engaged by the properly positioned seal/valving member, so that proper registry will always be achieved independently of the accuracy of the drive motor 26. However, it might be desirable to eliminate such pins and allow complete housing rotation; whereby positional controls of conventional design might be used with an accurate drive motor (such as a stepper motor) to bring the seal/valving member into proper registry. This construction and operation is illustrated in FIGS. 9A, 9B, 9C and 9D with the seal/valving member 31 positioned at four different operative position.

Figures 6A, 6B:
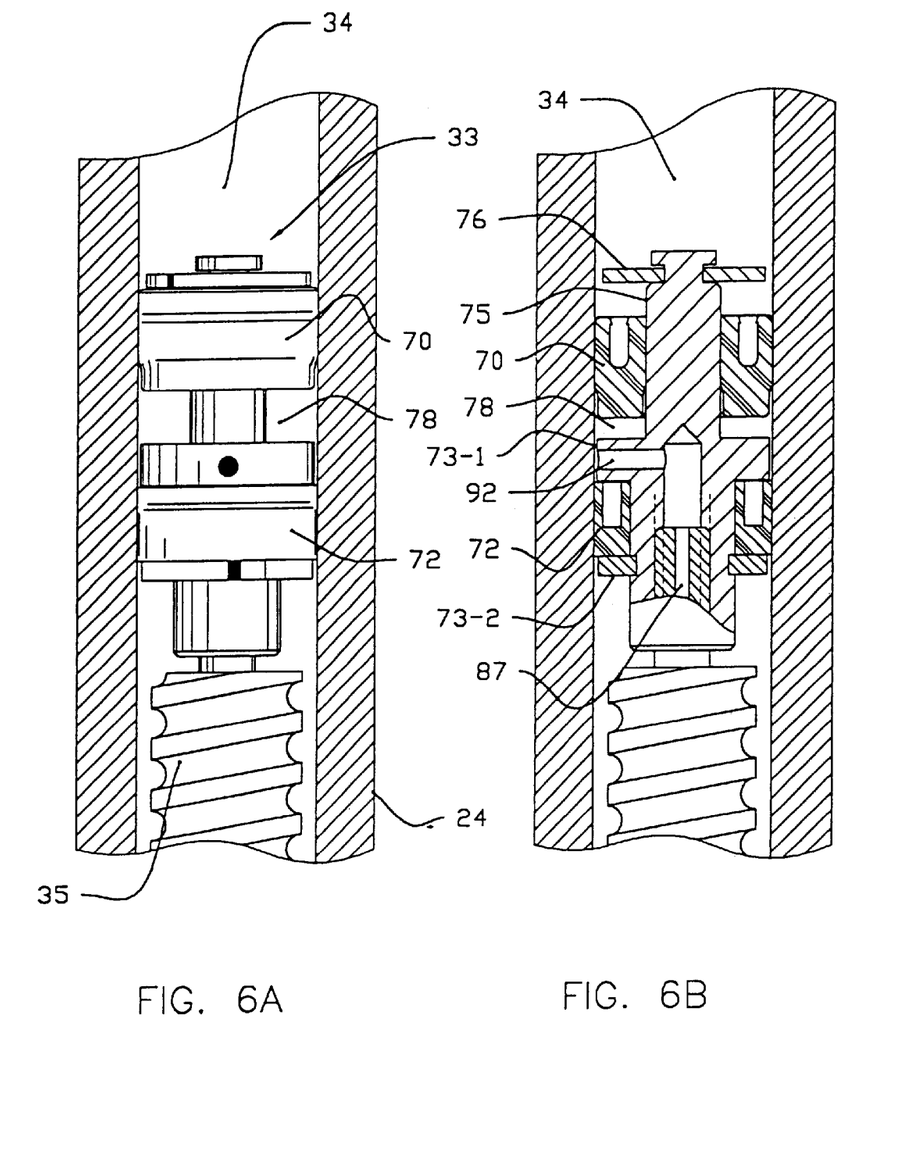
FIGS. 6A and 6B are views of the variable area pump plunger or piston, in different degrees of cross section and in different operative positions.
Figure 7:
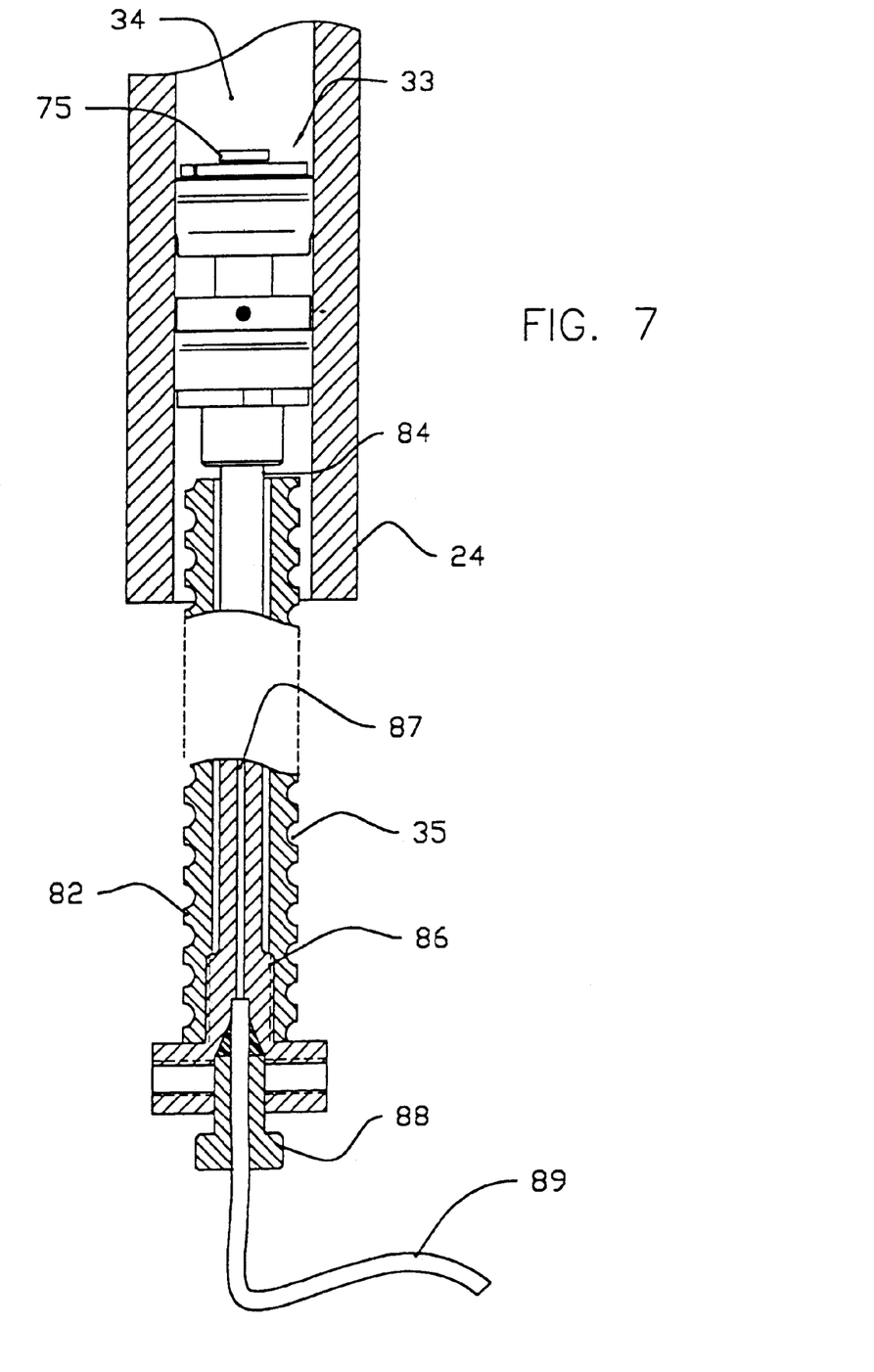
FIG. 7 is a center sectional view showing the piston of FIGS. 6A, 6B, extended to a tube flushing tube within the screw for flushing pump chamber, and extended to structure for keying the screw nonrotatably relative to the pump housing.

Of interest further, the piston assembly 33 disclosed herein (FIGS. 6A, 6B and 7) has axially spaced annular sealing regions 70 and 72 cooperating with the pump cylinder 24, sealing region 70 being immediately adjacent the defined pump chamber 34 and sealing region 72 being next to sealing region 70 but remote from the pump chamber 34. The sealing regions 70 and 72 can be formed of conventional annular spring seals. Further, sealing region 72 is fixed axially of the piston between plates 73-1 and 73-2 secured to or part of the screw stem 75, while sealing region 70 can axially slide sealingly along screw stem 75 between plate 76 secured to or part of the screw stem and at most to the plate 73-1, operable to define a variable volume chamber 78 between the sealing regions. However, this also changes the volume of the pump chamber 34 itself, but only according to the displacement provided by the changing amount of the screw stem 75 then being exposed within the pump chamber. Changing the volume of chamber 78 is useful in drawing a liquid solvent into and forcing it from the chamber 78 for flushing the cylinder housing walls; while changing volume of the pump chamber 34 at a reduced rate per similar axial piston travels is useful in more accurately drawing small quantities of the sample directly from the vial 12 into the control of pump, typically into the loop tubing 59, as the pump piston assembly 33 is being shifted downwardly from the position of FIG. 6A to that of FIG. 6B. The diffenence between the pumping capacities of only the screw stem 75 and the full sealing region 70 can be quite low, such as at a ratio of between 1:3 amd 1:10, making for more accurate sample drawing for the same axial suction pumping stroke.

Figure 9A:
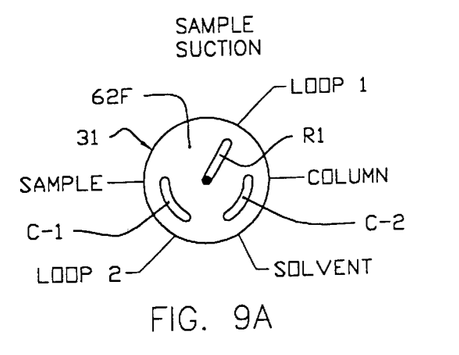
FIGS. 9A, 9B, 9C, 9D illustrate the grooved valve seat in different operative positions relative to the column, solvent, sample and loop ports.

By way of example, with the valving structure member 31 in the FIG. 9A position, increasing the volume of pump chamber 34 upon a downward stroke of the piston assembly 33 could be effective for drawing sample from the sample vial 12 via the reduced pressure or suction in the pump chamber, acting via bore 60, channel R-1 to the "loop-1" port, the exterior tubing 57 to the "loop-2" port, and the channel C-1 connection with the sample vial 12.

Figure 9B:
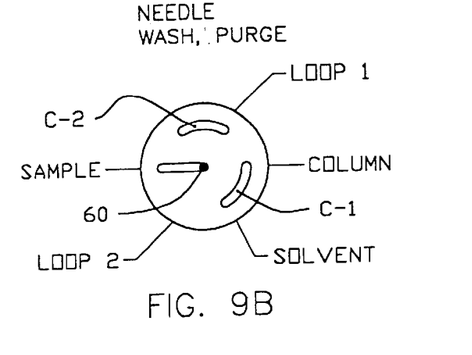

Further, with the valving structure member 31 in the FIG. 9B position, the needle that is inserted and/or positioned in the sample vial 12 can be flushed, as between runs testing different samples. The connection from the pump chamber 34 via bore 60 and radial channel R-1 is directly to the sample vial 12, for forcing solvent from the pump chamber 34 and through the needle upon upward movement of the piston assembly 33.

Figure 9C:
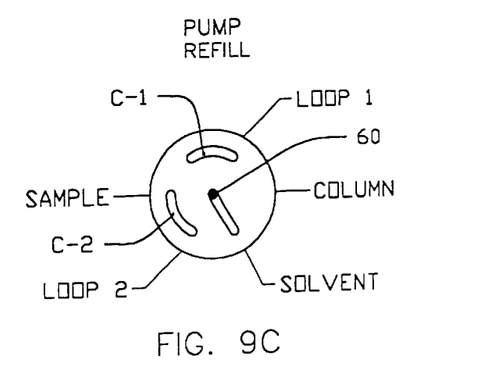

FIG. 9C corresponds to the pump chamber 34 refill cycle (of solvent) where the connection from the pump chamber 34 via bore 60 and radial channel R-1 is directly to the solvent bottle 16, for drawing solvent from the solvent bottle 14 upon downward movement of the piston assembly 33.

Figure 9D:
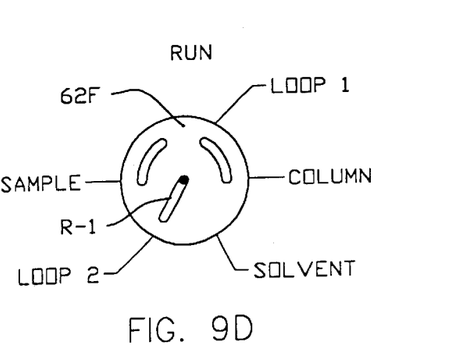
Figure 9E:
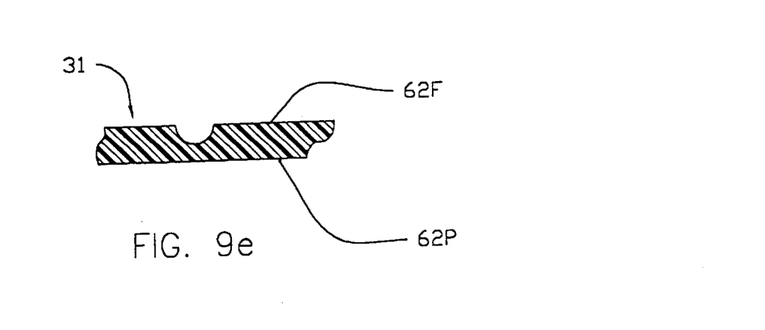
FIG. 9E is an enlarged sectional view of any representative groove.

FIG. 9D corresponds to the run or pumping and solvent delivery cycle, where the pump chamber communicates via bore 60, the channel R-1, "loop-2" port, the exterior tubing 57, the "loop-1" port, and the channel C-1 connection with the column 16 to deliver pressurized solvent and any sample in the exterior tubing 57 to the column upon upward movement of the piston assembly 33.

The formation of the screw 35 is also of importance, being comprised of an elongated threaded member 82 having a bore extended it entire length, and a smaller tubular member 84 fitted therein with radial clearance throughout except at connection 86 between the members 82, 84, which is at the end remote from the piston assembly 33 and near the cross pin 37. The inner tubular member 84 serves as the screw stem 75; and can be formed of stainless steel or durable plastic material suited to resist chemical attacks from any pumped solvent or cleaning liquid. Further, the inner tubular member bore 87 can be connected at fitting 88 to a flexible hose 89 that can communicate with a flushing liquid bottle 91. The bore can be continued upwardly to radial bore 92 (FIG. 6B) for communication with the flushing chamber 78. Thus, as the flushing chamber 78 is expanded and contracted, it can be continuously filled and depleted of flushing liquid, relative to the bottle 91, effective for flusing the cylinder housing bore walls. Also, this multiple piece assembly provides for ease of manufacture, without having to maintain with great difficulty any close concentric tolerances of the threaded screw as is needed as it cooperates, at greater or lesser degrees of projection away, from its drive member 40.

As the seating pressures between the mated moving and stationary components of the valving structure 20 are substantially proportional to the pumped liquid pressures (not bases on large fixed forces from springs or the like), and as the fluid pressures dissipate rapidly via the column 18 after a run cycle has been stopped, it will be possible to shift the valving structure without excessive valve structure wear.

Different groove configurations can be used on the mating valving structures, to satisfy other possible HPLC needs or interconnections, including connecting several pumps together for pumping several different solvents during any operating run.

The pump 10 as noted is powered by the reversible drive motors 26, 46, to shift the cylinder housing and connected valving structure 20 or the screw 35 and connected piston assembly 33 in opposite directions. Operation of these motors can be controlled as needed by conventional controls, including standard servo related controls. A single PC might control all pump operations, including the flow rates and pressures.

Reference has been made only of a single frame structure 22, but it is apparent that separate components can be used and assembled together to make up the unitary frame structure of the operative pump and valve assembly.

While specific embodiments have been illustrated and discussed, minor changes could be made in an overall assembly without departing from the spirit of the inventive teaching. Accordingly, the invention is to determined by the scope of the following claims.

What is claimed is:

1. A syringe pump and valve assembly for directing liquids from containment in respective reservoirs relative to yet another containment, comprising the combination of
    a frame structure, a pump, valving, and means supporting the pump and valving from the frame structure;
    said pump having a cylinder comprised of a housing having a longitudinal axis together with first and second ends and means supporting the cylinder housing to rotate concentrically of its longitudinal axis relative to the frame structure, an insertable seal/valving member closing the first end of the cylinder housing and being rotatable in unison therewith, a piston in sealed relationship in the cylinder housing whereby a variable volume pump chamber is defined at said first cylinder housing end as said piston is axially moved in the cylinder housing, means supported by the frame structure adjacent the second and open end of the cylinder housing for shifting the piston axially therewithin either in one direction effective to increase the chamber volume or in the opposite direction effective to decrease the pump chamber volume, and means for powering the piston shifting means;

said valving including said seal/valving member having a first face cooperating slidably with a stationary port seat on the frame structure and effective upon the occurrence of cylinder housing rotation to be shifted selectively to different operating positions effective: for isolating either or both reservoirs, for communicating either reservoir to the pump chamber, and/or for communicating the pump chamber to the other containment;

said seal/valving member having a second face opposite said first face, and said second face being exposed to the pump chamber, whereby pumped fluid pressures in the pump chamber bias the seal/valving member first face against the frame structure port seat with seating pressures proportional to the pumped pressures; and means operable independently of the means powering the piston shifting means to shift said cylinder housing and coupled seal/valving member to said different operative positions.

2. The pump and valve assembly according to claim 1, further with said insertable seal/valving member having a narrow wall lip formed off of the opposite face sized to be pressed tightly into the cylinder housing and to have a small overlap therewith.

3. The pump and valve assembly according to claim 1, further comprising said piston having a slidable sealing region of a first area with the pump cylinder, a stem having a sliding sealed cooperation with the piston and being of significantly smaller area than the first area, and said stem being shiftable axially relative to the piston to extend into the pump chamber, operable to modify the volume change of the pump chamber upon unit piston movement in the cylinder housing.

4. The pump and valve assembly according to claim 3, further comprising said piston having a second sealing region axially spaced from and remotely of the pump chamber from the first mentioned sealing region, means supporting said first and second sealing regions to be axially movable relative to the one another to provide a flushing chamber therebetween of variable volume, a source of cleaning liquid located remote from the flushing chamber, and means communicating the flushing chamber to said cleaning liquid source operable to have the cleaning liquid therein during piston movement.

5. The pump and valve assembly according to claim 4, further wherein said means for shifting the piston axially within the cylinder housing comprises a drive member rotatably supported by the frame structure adjacent the open end of the cylinder housing and a screw cooperating with the drive member operable to be shifted axially as said drive member is rotated, said screw being extended axially of the cylinder housing in the direction away from the pump chamber, and said means communicating the flushing chamber to said cleaning liquid source being within an axial bore in said screw.

6. The pump and valve assembly according to claim 1, further wherein said means for shifting the piston axially within the pump cylinder comprises a drive member rotatably supported by the frame structure adjacent the open end of the cylinder housing and a screw cooperating therewith to be shifted axially of the cylinder housing as said drive member is rotated, said screw having a near end and a far end and having a bore extended to the piston, a separate elongated member fitted in the axial screw bore with radial clearance and connected to and supporting the piston in the region of the near end, and means connecting the separate member and screw together only at the two far ends thereof remote from the piston and pump chamber.

7. A syringe pump for directing liquids from containment in respective reservoirs to yet another containment, comprising the combination of a frame structure;

a pump having a cylinder comprised of a housing having a longitudinal axis together with a closed end and an opposite open end and means supporting the cylinder housing to rotate concentrically of its longitudinal axis relative to the frame structure;

a piston in sealed relationship in the cylinder housing and defining a pump chamber adjacent the closed end of the cylinder housing; and means axially shifting the piston within the cylinder housing for varying the pump chamber volume, said shifting means being comprises of a drive member rotatably supported by the frame structure adjacent the open end of the cylinder housing and a screw cooperating with said drive member to be shifted axially of the cylinder housing as said drive member is rotated, said screw having a near end and a far end and having a bore extended to the piston in the region of the near end, a separate elongated member fitted in the screw bore and having radial clearance from the screw at the near end thereof and being connected to and supporting the piston, and means connecting the separate elongated member and screw together only at the two far ends thereof remote from the piston and pump chamber.

8. A syringe pump and valve assembly comprising a cylindrical housing having a longitudinal axis and having opposite first and second ends, and means supporting the housing to rotate concentrically of its longitudinal axis, a piston fitted in sealed relationship in the housing and adapted to be moved axially therein, a seal/valving member for closing the first end of the housing, whereby a variable volume pump chamber is adapted to be defined in the housing between the seal/valving member and piston, a port seat spaced from the first end of the housing and disposed concentrically of the housing longitudinal axis and a plurality of separate ports on said port seat, connector means for the communication of separate fluid lines to said respective separate ports on the port seat, said seal/valving member having a first face adapted to cooperate slidably on the port seat and a second oppositely directed face exposed to the pump chamber, with said first face being adapted to overlie the separate ports on the port seat and operable to be biased against the port seat with forces proportionally related to fluid pressures in the pump chamber, said seal/valving member also having means between the first and second faces effective in different operative seal/valving member positions for selectively providing isolation and/or communication of the fluid lines relative to one another and/or the pump chamber, means to rotate in unison the housing and seal/valving member operable to position said first face of the seal/valving member selectively in the above-noted different operative positions relative to the port seat, and means adjacent the second end of the cylinder housing for moving the piston and varying the volume of the pump chamber whereby fluids selectively might be drawn into and/or pumped away from the pump chamber.

9. A pump and valve assembly according to claim 8, further wherein the means between the first and second faces of the seal/valving member for selectively isolating or communicating the fluid lines relative to one another and/or the pump chamber comprising the seal/valving member having a blocking structure for providing the above-noted isolation, or having through opening and arcuate or radial channels extended between different ports for providing the above-noted communication.

\* \* \* \* \*